(12) United States Patent
Muguruma et al.

(10) Patent No.: US 7,087,149 B1
(45) Date of Patent: Aug. 8, 2006

(54) BIOSENSOR

(75) Inventors: Hitoshi Muguruma, Chiba (JP); Atsunori Hiratsuka, Tokyo (JP); Isao Karube, Kanagawa (JP)

(73) Assignee: Katayanagi Institute, Tokyo (JP)

( * ) Notice: Subject to any disclaimer, the term of this patent is extended or adjusted under 35 U.S.C. 154(b) by 0 days.

(21) Appl. No.: 09/958,671

(22) PCT Filed: Apr. 13, 2000

(86) PCT No.: PCT/JP00/02417

§ 371 (c)(1),
(2), (4) Date: Jan. 8, 2002

(87) PCT Pub. No.: WO00/63685

PCT Pub. Date: Oct. 26, 2000

(30) Foreign Application Priority Data

Apr. 15, 1999 (JP) ................. 11-107691

(51) Int. Cl.
G01N 27/327 (2006.01)
C08F 2/46 (2006.01)
C12Q 1/00 (2006.01)

(52) U.S. Cl. .............. 205/778; 204/403.1; 204/403.11; 427/58; 427/488

(58) Field of Classification Search ........... 204/403.05, 204/403.06, 403.07, 403.1, 403.11; 205/777.5, 205/778; 427/58, 488
See application file for complete search history.

(56) References Cited

U.S. PATENT DOCUMENTS 4,897,305 A * 1/1990 Ho .............................. 428/333
6,156,173 A * 12/2000 Gotoh et al. ........... 204/403.04
6,627,397 B1 * 9/2003 Nakamura et al. ............. 435/6

FOREIGN PATENT DOCUMENTS

| JP | 60-006193 | 1/1985 |
| JP | 61-091558 | 5/1986 |

(Continued)

OTHER PUBLICATIONS

Steward et al, "Improved adhesion of thin conformal films to metal surfaces", Gov. Rep. Announce. Index (U.S.) 1986, 86(20), Abstr. No. 645,213 (CAS abstract only).*

(Continued)

Primary Examiner—Kaj K. Olsen
(74) Attorney, Agent, or Firm—Banner & Witcoff Ltd.

(57) ABSTRACT

A novel biosensor was accomplished using a plasma-polymerized membrane. The biosensor of the present invention is a high-performance biosensor produced by a simpler method and applicable to a wide range of fields.

17 Claims, 6 Drawing Sheets

FOREIGN PATENT DOCUMENTS

| JP | 02-061549 | 3/1990 |
|---|---|---|
| WO | WO 94/04241 | 3/1994 |
| WO | WO 01/33227 A1 | 5/2001 |

OTHER PUBLICATIONS

Anal. Lett., 22(11/12) p. 2423-2431 (1989), p. 2425 1.7-p. 2426 1.19 & Fig. 1.

Microchem. J., 53 (2) p. 207-214 (1996).

ASS Symp. Ser. (Am Chem Soc), No. 690 p. 57-65 (1998).

Hiratsuka, et al. "Mass transport behavior of eletrochemical species through plasma-polymerized thin film on platinum electrode", Journal of Membrane Science, 2000, pp. 25-34, vol. 175, Elsevier.

Miyachi, Hirotaka et al., "Application of Polymer-Embedded Proteins to Fabrication of DNA Array", Biotechnology and Bioengineering, vol. 69, No. 3, Aug. 5, 2000, pp. 323-329.

Yoshimura, K, et al., "Preparation of Immobilized Glucose Oxidase Membrane by the Plasma Ploymerization Technique", Microchemical Journal, vol. 43, pp. 133-142, 1991.

Hiratsuka A. et al., "A Glucose Sensor with a Plasma-Polymerized Thin Film Fabricated by Dry Processes", Electroanalysis, 11(15), 1999, pp. 1098-1100.

European Patent Office, International Search Report, Supplementary European Search Report, EP 00 91 5512, Dec. 3, 2002.

Hitoshi Muguruma et al., "Thin-Film Glucose Biosensor Based on Plasma-Polymerized Film: Simple Design for Mass Production", Anbalytical Chemistry, vol. 72, No. 11, 2000, pp. 2671-2675.

Everhart, Dennis S. & Reilley, Charles N., "Chemical Derivatization in Electron Spectroscopy for Chemical Analysis of Surface Functional Groups Introduced on Low-Density Polyethylene Film", Anal. Chem. 1981, 53(4), pp. 685-676.

Muguruma, Hitoshi, et al., "Sulfur Containing Plasma Treatment for the Introduction of Thiol Groups onto Polyethylene Surfaces", Chemistry Letters, 1996, pp. 283-284.

* cited by examiner

Cross section (X-X')

BIOSENSOR

This is a U.S. National Phase Application Under 35 USC 371 of PCT/JP00/02417 filed Apr. 13, 2000, which was published under PCT Article 21(2) in Japanese. Applicant claims the benefit of Application No. JP 11/107,691 filed in Japan on Apr. 15, 1999.

TECHNICAL FIELD

This invention relates to biosensors in which catalytic components such as enzymes are immobilized and to the utilization of such biosensors.

BACKGROUND ART

Biosensors using catalytic substances such as enzymes are being applied, not only in the analysis of glucose, but also in the analysis of various other ingredients. Such biosensors are capable of measuring various enzyme substrates precisely and easily by using minute amounts of enzymes. As opposed to traditional enzyme reactions that take place in solutions, biosensors are considered to have large economical and operational advantages as analysis systems. Among biosensors using enzymatic activity, glucose sensors are the most widely used.

Patients with diabetes, one of the adult diseases, need to measure their blood sugar level several times a day and take insulin and control the diet according to the readings. This makes glucose sensors essential for diabetic patients, as it enables easy measurement of blood glucose concentration. Glucose sensors can also be useful tools in the fields of medicine and food industry.

The glucose sensor currently available in the market was developed by Matsushita Electric Industrial Co., Ltd. This glucose sensor consists of electrodes on which an enzyme, glucose oxidase (hereafter occasionally referred to as GOD), is immobilized. In practical use, a drop of the patient's blood is placed on the sensor tip, and the blood glucose level is determined quickly after inserting the tip into a measuring device. Descriptions of this kind of glucose sensors are seen in unexamined Published Japanese Patent Application No. (JP-A) Hei 1-253648, Examined Published Japanese Patent Application No. (JP-B) Hei 5-24453, JP-A Hei 6-213858, JP-A Hei 1-156658, JP-B Hei 6-58338, JP-A Sho 63-139243, etc.

The sensor tips of these glucose sensors are fabricated by applying a solution containing glucose oxidase, potassium ferricyanide and carboxymethyl cellulose, on a silver- or carbon-paste electrode pattern printed on a board, and drying it. Potassium ferricyanide, which composes the sensor tip, is called the mediator; it is the substance that acts as an intermediary between the electrons generated through the enzymatic reaction and the electrodes. When a test solution is dropped onto the surface of the sensor tip, a reaction as in [1] below is initiated. Then, the reduced enzyme reacts with potassium ferricyanide to result in a reaction as in [2], wherein potassium ferricyanide and potassium ferrocyanide are the oxidized and reduced molecular species of each other, respectively. Lastly, the reduced mediator causes an oxidative reaction as in [3] on the electrode. Glucose level is determined by measuring this oxidation current.

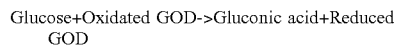   [1]

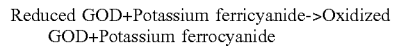   [2]

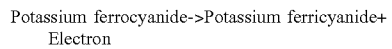   [3]

The mediator that supports the above reactions has major roles as follows: First, it suppresses effects of other components in the test material. For example, blood contains reductive components such as ascorbic acid (vitamin C) and uric acid and they interfere with the detection of oxidation current generated by the enzymatic reaction. Use of a mediator reduces applied voltage at the time of current measurement and consequently reduces effects of interfering reductive substances. A second role of the mediator is to facilitate a sufficient enzyme reaction. Occasionally, blood of a diabetic patient shows a very high level of glucose. With a limited amount of dissolved oxygen, the high level glucose may not be sufficiently oxidized. The mediator helps enzyme-mediated glucose oxidation and thus lowers the effect of dissolved oxygen when measuring a high-level of blood glucose.

Thus, a glucose sensor using GOD is supported by the actions of the mediator. However, some problems have been pointed out concerning mediators. Low molecule weight mediators used for mediator-type biosensors are difficult to immobilize completely. Therefore, although they are claimed to be immobilized, detachment from the electrode is occasionally observed after long-term use. This makes mediator-type biosensors unsuitable for continuous use. Further, some compounds used for mediators such as ferricyanides exhibit toxicity at high concentrations. Ferrocenes, another group of compounds used for mediators, are suggested to have the danger of being poisonous due to iron deposition through the detachment. Thus, they are unsuitable for use in indwelling sensors. The risk of detachment of the immobilized substance in indwelling-type biosensors has been pointed out also regarding materials other than mediators. A detached enzyme, for example, may be recognized as a heterogenous protein and induce an allergic reaction.

In manufacturing, the use of mediators accompanies problems in uniformity of the membrane, reproducibility, adherability to the electrode, and yield ratio. That is, with the method in which the enzyme and mediator are applied onto the electrode with a carboxymethyl cellulose membrane, it is difficult to maintain a high uniformity. Further, the difficulty to maintain uniformity makes mediator-type biosensors unsuitable for compact, inexpensive sensors.

Besides biosensors using catalytic substances like enzymes those making use of reactions based on affinity between substances are also known. The former is called catalytic biosensors and the latter affinity biosensors. Representative examples of affinity biosensors are immunosensors that utilize the antigen-antibody reaction and gene sensors that utilize the affinity between nucleic acids with complementary nucleotide sequences. For immobilization of antibodies or genes in affinity biosensors, a method utilizing functional groups on the plasma-polymerized membrane applied on the sensor surface is known (Trend in Analytical Chemistry Vol. 18, pp 62–68, 1999). Functional groups accumulate at a high density on the surface of a plasma-polymerized membrane, and thus it is believed that proteins can be immobilized at a high density.

On the other hand, a catalytic biosensor with a structure of plasma-polymerized membranes overlaid on a semiconductor surface has been reported (Analytical Letters, 22, 2423–2431, 1989). In this report, although a plasma-polymerized membrane is used, the membrane is formed only on the top of the semiconductor, leaving the semiconductor pattern exposed in the cross sectional direction because a mask similar to the semiconductor pattern is used for the membrane formation. Contaminants contained in the test material affect the exposed semiconductor directly, interfering with the electrical measurement.

DISCLOSURE OF THE INVENTION

An objective of the present invention is to provide, without using a mediator, a biosensor that is not easily affected by coexisting interfering substances and can accomplish a superior response. Another objective of the present invention is to provide a biosensor in which the immobilized catalytic substance does not easily detach even after repeated or continuous use. In addition, the present invention aims to provide a biosensor that takes advantage of a characteristic of semiconductor processing technologies, which is excellent mass-productivity.

A general catalytic biosensor is comprised of a combination of an enzyme and an electrode. It can be said that the characteristics of the sensor depend on how effectively the catalytic substance is immobilized on the electrode surface. Immobilization of enzymes onto the electrode surface is referred to as "enzyme immobilization techniques" or "interface design". In an attempt to introduce a new interface design to resolve the above-mentioned issues, the inventors of the present invention confirmed that use of plasma-polymerized membranes in the interface design allows high-level accumulation of the catalytic substance or enables application of semiconductor processing technologies. Further, in completing th present invention, the inventors discovered that the plasma-polymerized membrane is useful as a new interface that does not require mediators, which are essential to conventional catalytic biosensors. Namely, the present invention relates to the following:

(1) a biosensor comprising the following elements:

a) a plasma-polymerized membrane, b) a catalytic substance immobilized on the plasma-polymerized membrane, and, c) a metal electrode pattern in contact with a test material via the plasma-polymerized membrane;

(2) the biosensor according to (1), wherein the metal electrode pattern is formed on the plasma-polymerized membrane and said metal electrode pattern comprises an additional plasma-polymerized membrane on top;

(3) the biosensor according to (1), wherein the catalytic substance is covalently bound onto the plasma-polymerized membrane with a crosslinking agent;

(4) the biosensor according to (1), wherein the catalytic substance is an enzyme;

(5) the biosensor according to (4), wherein the enzyme is either an oxidase or a dehydrogenase;

(6) the biosensor according to (5), wherein the oxidase is selected from the group consisting of glucose oxidase, galactose oxidase, pyruvate oxidase, D- or L-amino acid oxidase, amine oxidase, cholesterol oxidase, and choline oxidase;

(7 the biosensor according to (5), wherein the dehydrogenase is selected from the group consisting of alcohol dehydrogenase, glutamic acid dehydrogenase, cholesterol dehydrogenase, aldehyde dehydrogenase, glucose dehydrogenase, fructose dehydrogenase, sorbitol dehydrogenase, and glycerol dehydrogenase;

(8) the biosensor according to (1), wherein the plasma-polymerized membrane contains one or more functional groups selected from the group consisting of —COOH, —CHO, —SH, —NH$_2$, —OH, =NH, —CONH$_2$, —NCO, —CH=CH$_2$, =C=O and

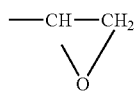

groups;

(9) the biosensor according to (1), comprising a multi-layer structure with two or more layers of plasma-polymerized membranes;

(10) the biosensor according to (1), wherein the plasma-polymerized membrane is overlaid with a second plasma-polymerized membrane with polymeric or non-polymeric monomer materials;

(11) the biosensor according to (1), wherein the above-mentioned non-polymeric monomer material is selected from the group consisting of nitrogen, ammonia, hydrazine, hydrogen sulfide, hydrogen disulfide, oxygen, hydrogen, water, halogen gas and rare gas;

(12) a method to measure a substrate component using a catalytic substance, wherein the biosensor comprises (i) a metal electrode pattern that contacts the test material via a plasma-polymerized membrane and (ii) a catalytic substance immobilized on the plasma-polymerized membrane, and wherein said method comprises the following steps of:

a) contacting the test material with the biosensor in which the catalytic substance is immobilized, and, b) detecting the electrical changes associated with the reaction between the catalytic substance and substrate using electrodes.

Plasma polymerization is a technique to form a membrane directly on a board surface by plasma excitation of a monomer gas in a vacuum. FIG. 1 shows a typical plasma polymerization system. Plasma-polymerized membranes with different characteristics are obtained depending on components of the monomer gas. In principle, any monomer may be used to accomplish polymerization in plasma polymerization. This is because monomer gas disperses in plasma to cause polymerizing reactions via a number of activated species, in contrast to ordinal polymerization that requires splitting of double bonds. As compounds used as monomer gas, it is advantageous to use those that supply appropriate functional groups when forming the polymerized membrane so that the catalytic substance can be chemically bound by using the functional groups. The functional groups include —COOH, —CHO, —SH, —NH$_2$, —OH, =NH, —CONH$_2$, —NCO, —CH=CH$_2$, =C=O, and

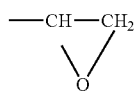

groups. Examples of monomer gas compounds that can supply a plasma-polymerized membrane with these functional groups are described blow. Namely, nitrogen- and sulfur-containing compounds, hydrocarbon compounds containing oxygen, etc. With excellent adhesiveness to the surface of commonly used board materials such as glass and silicon, these compounds are suitable for the present invention.

Nitrogen-Containing Compounds

Nitrogen-containing compounds include those comprising carbon (C), hydrogen (H) and nitrogen (N) and have one or more double or triple bonds, such as nitrogen, pyridine, allylamine, acrylamide, aniline, allylnitrile, 1,2,4-triazol, 5-amino-1H-tetrazole, propargylamine, etc. In addition, compounds expressed by the following general formulas may be used. A representative compound for each general formula is given below within parenthesis. Nitrogen-containing compounds supply the surface of the plasma-polymerized membrane with amino groups that can be used for chemically binding catalytic substances. The surface and inside of the membrane are hydrophilic; the affinity to an aqueous specimen such as blood makes the membrane a favorable material having characteristics suitable for a biosensor.

Compounds expressed by the general formula: $CH_3-(CH_2)_n-NH_2$ (wherein "n" is an integer between 1 and 6) (ethylamine, etc.)

Compounds expressed by the general formula: $(CH_3)_3(CH_2)_n N$ $\{n \geq 0\}$ (triethylamine $(C_2H_5)_3N$, etc.)

Compounds expressed by the general formula: $(CH_3)_2(CH_2)_n NH$ $\{n \geq 0\}$ (diethylamine $(C_2H_5)_2NH$, etc.)

Compounds expressed by the general formula: $CH_2=CH(CH_2)_n NH_2$ $\{n \geq 0\}$ (allylamine $CH_2=CHCH_2 NH_2$, etc.)

Compounds expressed by the general formula: $CH_3(CH_2)_n CN$ $\{n \geq 0\}$ (acetonitrile $CH_3CN1$ etc.)

Compounds expressed by the general formula: $NH_2-(CH_2)_n-NH_2$ (wherein "n" is an integer between 1 and 6) (ethylenediamine, hexamethylenediamine, etc.)

In addition, nitrogen-containing monomer gas compounds include the following:

RaNRb$_2$

Wherein Ra and Rb are alkyl chains selected from the group consisting of H, $CH_3(CH_2)_n$ $\{n \geq 0\}$, alkyl chain comprising a double bond or a triple bond or both within the chain, and branched or cyclic alkyl chain.

RaNRc

Wherein Rc is an alkyl chain selected from the group consisting of H, $CH_3(CH_2)$ CH $\{n \geq 0\}$, $CH_2$, alkyl chain comprising a double bond or a triple bond or both within the chain, and branched or cyclic alkyl chain.

RdN

Wherein Rd is an alkyl chain selected from the group consisting of H, $CH_3(CH_2)_nC$ $\{n \geq 0\}$, CH, alkyl chain comprising a double bond or a triple bond or both within the chain, and branched or cyclic alkyl chain.

RaNReNRa$_2$

Wherein Ra is the same as the above-mentioned alkyl chain, and Re is an alkyl chain selected from the group consisting of H, $(CH_2)_n$ $\{n \geq 0\}$, alkyl chain comprising a double bond or a triple bond or both within the chain, and branched or cyclic alkyl chain.

RfNRgNRh

Wherein Rf and Rg are alkyl chains selected from the group consisting of H, $CH_3(CH_2)_n$ $\{n \geq 0\}$, $CH_3(CH_2)_nCH$, $\{n \geq 0\}$, $CH_2$, alkyl chain comprising a double bond or a triple bond or both within the chain, and branched or cyclic alkyl chain.

Rh is an alkyl chain selected from the group consisting of H, $CH_3(CH_2)$ {n-O}, $CH_3(CH_2)_n$ CH $\{n \geq 0\}$, $CH_3 (CH_2)_nC$ $\{n \geq 0\}$, CH, alkyl chain comprising a double bond or a triple bond or both within the chain, and branched or cyclic alkyl chain.

NRiN

Wherein Ri is an alkyl chain selected from the group consisting of $CH_3(CH_2)_nC$ $\{n \geq 0\}$, comprising a double bond or a triple bond or both within the chain, and branched or cyclic alkyl chain.

Sulfur-Containing Compounds

Sulfur-containing compounds include hydrogen sulfide, hydrogen disulfide, thiophene and those expressed by the general formula $CH_3S(CH_2)_nCH3\{n \geq 0\}$. An example of such compounds is dimethyl sulfide$(CH_3)_2S$. Compounds expressed by the general formula $CH_3(CH_2)_nSS(CH_2)_mCH_3$ $\{m, n \geq 0\}$ are also included. An example of such compounds is methyl disulfide $CH_3SSCH_3$. Compounds expressed by the general formula $CH_3(CH_2)_nSH$ $\{n \geq 0\}$ are also included. An example of such compounds is ethanethiol $CH_3CH_2SH$. Further, Compounds expressed by the general formula $SH(CH_2)_nSH$ $\{n \geq 1\}$ are also included. An example of such compounds is ethanedithiol $SH(CH_2)_2SH$.

Other sulfur-containing compounds include thiophene, mercaptoethanol dithreitol, and so on. These sulfur-containing compounds, like nitrogen-containing compounds, make the surface and inside of the membrane hydrophilic and provide thiol groups to the surface, which facilitate chemical bonding of catalytic substances Oxygen-Containing Hydrocarbon Compounds Oxygen-containing compounds include methanol, ethanol, propanol, butanol, formic acid, acetic acid, propionic acid, acetaldehyde, benzaldehyde, acrolein, acrylic acid, methacrylic acid, methyl methacrylate, propargyl alcohol, acetone methyl ethyl ketone, and so on. Plasma-polymerized membranes obtained from these compounds are hydrophobic inside. This is because oxygen atoms show the characteristic of not being easily taken up into the membrane at the time of plasma-polymerized membrane formation. This gives the inside of the membrane a structure similar to that of the hydrocarbon plasma-polymerized membrane (i.e. a hydrophobic structure). The surface of the membrane has oxygen-containing functional groups, such as carboxyl, carbonyl, aldehyde, and hydroxyl groups.

There are also materials for monomer gas compounds that do not have functional groups usable for chemical bonding but provide plasma-polymerized membranes useful for physical adsorption of catalytic substances. Such materials include silicon-containing compounds, hydrocarbon compounds, halogen gases, rare gases, and so on as follows:

Organic Silicon Compounds

Organic silicon compounds include tetramethylsilane, tetramethyldisiloxane, hexamethyldisiloxane; hexamethyldisilazane, hexamethylcyclotrisilazane, diethylaminotrimethylsilane, trimethylvinylsilane, tetramethoxysilane, aminopropyltriethoxysilane, octadecyldiethoxymethylsilane, hexamethyldisilane and divinyltetramethyldisiloxane.

Hydrocarbon compounds include compounds and such containing an —OH group, such as propargyl alcohol.

Rare gases such as argon, neon, helium, krypton and xenon can also be used as the monomer gas materials.

These monomer gases may be used alone or in a mixture of two or more monomer gases. Also, the structure may be single layer or multilayer with a second plasma-polymerized membrane. Polymeric or non-polymeric material may be used for the second plasma-polymerized membrane. For example, amino groups can be introduced to the membrane surface by treating the first plasma-polymerized membrane using a non-polymeric monomer gas, such as ammonia. By utilizing a second plasma-polymerized membrane, desired functional groups can be introduced without altering materials of the board.

Plasma polymerization conditions, i.e., flow rate of the monomer gas, discharge power of plasma, pressure of reaction atmosphere, and reaction time, can be set appropriately by one skilled in the art in accordance with the monomer gas used. For example, when using a nitrogen-containing compound such as hexamethyldisiloxane or acetonitrile as the monomer gas as described in the Examples, conditions may be set as follows: flow rate: 10 to 50 $cm^3$/min., discharge power: 20 to 100 W, pressure: 1 to 10 Pa, discharge time: 30 sec. to 5 min. For plasma polymerization, optimal polymerization conditions should be set in accordance with the device and the monomer used. It has been reported that the same W/FM value (Wherein W is discharge power, F is flow rate, and M is molecular weight of monomer) yields almost the same membranes (Yasuda, Plasma Polymerization, Academic Press, New York, 1985).

In the present invention, the plasma-polymerized membrane functions not only to support immobilization of catalytic substances but also as a selective membrane to selectively supply signal-generating substances to the underlying metal electrode pattern. For this reason, the present invention requires a structure in which the plasma-polymerized membrane prevents the specimen from directly coming into contact with the metal electrode pattern; the metal electrode pattern and the specimen must contact only through the plasma-polymerized membrane. Such a structure can be obtained for example by covering the surface of the board that contains a metal electrode pattern with a plasma-polymerized membrane, as described in the Examples. Or, the etching method may be used to cover the exposed metal pattern with a plasma-polymerized membrane. Use of plasma polymerization can facilitate complete coating of complex and small structures with a uniform plasma-polymerized membrane. Thus, the plasma-polymerized membrane has highly advantageous features for coating of metal electrode patterns, which often involve small and complex shapes.

Signal-generating substances as used herein refer to substances capable of generating electrical signals by electrode reactions with the metal electrode pattern. In the present invention, the signal-generating substances are generated by actions of catalytic substances bound to the surface of the plasma-polymerized membrane. For example, when a compound such as glucose oxidase is immobilized, $H_2O_2$ generated by the oxidation of glucose corresponds to the signal-generating substance. The plasma-polymerized membrane selectively passes and supplies $H_2O_2$ to the metal electrode pattern. Because the plasma-polymerized membrane is dense, even a membrane so thin as 100 nm has a size-exclusion effect, and passes low molecular weight compounds including $H_2O_2$ while reducing effects of interfering substances. The membrane should preferably be thick enough to provide a sufficient size-exclusion effect. On the other hand, a thinner membrane provides faster response. Thus, the two have a trade-off relationship. Optimal membrane thickness, although it depends on the type of monomer gas used, is 50 to 200 nm in general. In the present invention, due to the selective characteristic of the plasma-polymerized membrane for the signal-generating substances, effects of interfering substances can be avoided without using a mediator. In addition, the plasma-polymerized membrane of the present invention not only prevents transmission of interfering substances, but also functions as a selective membrane for signal-generating substances such as $H_2O_2$. That is, the presence of the plasma-polymerized membrane enhances response to $H_2O_2$.

In the present invention, the plasma-polymerized membrane is allocated over the metal electrode pattern. There are no specific limitations to the metal electrode pattern as long as it is made of materials that allow electrochemical reactions, such as platinum, gold, silver and graphite. Among them, platinum reacts best with $H_2O_2$ and thus is most suitable. The masking method is most suitable for forming the metal electrode pattern, while etching is not suitable. Recommended thickness of the metal electrode pattern is 100–1000 nm.

For the board on which the metal electrode pattern is formed, use of materials that also allow formation of plasma-polymerized membranes is recommended. Glass, plastic, silicon or cellulose and such can be recommended as general board materials. Although glass boards have poor compatibility with noble metals such as platinum, adhesion is expected to increase by forming a plasma-polymerized membrane first and then forming a thin platinum membrane. Then, by applying a plasma-polymerized membrane over the thin platinum membrane, a biosensor of the present invention is achieved. A preferred embodiment of the present invention is a biosensor with a plasma-polymerized membrane applied first onto a board of desired material, a metal electrode pattern formed over the membrane, and another plasma-polymerized membrane applied over the pattern (FIG. 2). To apply a thin platinum membrane over the plasma-polymerized membrane, it is advantageous to make the membrane using such monomer gases as organic silicon compounds that have high adhesiveness to glass or silicon. The organic silicon compounds include tetramethylsilane, tetramethyldisiloxane, hexamethyldisiloxane; hexamethyldisilazane, hexamethylcyclotrisilazane, diethylaminotrimethylsilane, trimethylvinylsilane; tetramethoxysilane, aminopropyltriethoxysilane; octadecyldiethoxymethylsilane, hexamethyldisilane; divinyltetramethyldisiloxane and so on. The minimum thickness for the plasma-polymerized membrane is 10 nm. Although a method to apply an approximately 5 nm-thick chrome layer to enhance adhesive of the platinum pattern to the glass board is known, chrome occasionally alloys with platinum, resulting in abnormal electrochemical signals.

In the present invention, a catalytic substance is immobilized on the plasma-polymerized membrane. Enzymes such as oxidases and dehydrogenases are used as catalytic substances. Oxidases that can be used as catalytic substances include:

glucose oxidase, galactose oxidase, pyruvate oxidase,

D- or L-amino acid oxidase, amine oxidase, cholesterol oxidase, and choline oxidase.

Dehydrogenases that can be used as the catalytic substance include:

alcohol dehydrogenase, glutamate dehydrogenase, cholesterol dehydrogenase, aldehyde dehydrogenase, glucose dehydrogenase, fructose dehydrogenase, sorbitol dehydrogenase, and glycerol dehydrogenase, etc.

These oxidases and dehydrogenases are suitable enzymes for the present invention in that they can directly detect oxidation (or reduction) of the substrate as electrical changes. Oxidase-based enzyme reactions are electrically detected through generation of $H_2O_2$. With dehydrogenases, coenzymes such as nicotinamide adenine dinucleotide (NAD) or nicotinamide adenine dinucleotide phosphate (NADP) function as electron acceptors, and increases and decreases in reduced molecular species (such as NADH and NADPH) of the coenzymes are electrically detected though electrode reactions.

The catalytic substance may be bound and fixed to the surface, or embedded inside the plasma-polymerized membrane. Embedding of the catalytic substance is achieved as follows. A plasma-polymerized membrane is formed over the board using a desired monomer gas. Oxygen or argon is most commonly used as the monomer gas. Then, the board is immersed in a solution containing a catalytic substance such as an enzyme, a monomer such as methacrylic acid, and acrylamide. Due to the presence of activated species on the surface of the plasma-polymerized membrane on the board, the monomers in the solution begin polymerization. In this process, the catalytic substance coexisting in the solution is embedded. This technique is called plasma-initiated polymerization (Plasma Polymerization, Tokyo Ragaku Dozin, 1986). In case an enzyme is embedded, the plasma-polymerized membrane that contacts the specimen must be permeable to the substrate. The catalytic substance to be bound may be one enzyme, or a combination of several enzymes. To electrically detect reactions involving several enzymes, required catalytic substances might be combined and immobilized at such ratios as to optimize the efficiency of the reaction processes.

Preferably, the catalytic substance is immobilized on the plasma-polymerized membrane formed on the metal electrode pattern. Such a structure locates them close enough to each other allowing a signal-generating substance like $H_2O_2$ that is generated by the catalytic substance to be easily provided to the metal electrode pattern, and thus likely improving response characteristics. Methods to immobilize enzymes on the plasma-polymerized membrane include physical adsorption and use of crosslinking agents. The latter is more useful to immobilize a large amount of enzymes stably. In this case, the functional groups on the surface of the plasma-polymerized membrane and those of the enzymes are bound with known crosslinking agents. Examples of crosslinking agents that can be used for the present invention are listed below, among which the most preferred is glutaraldehyde for its versatility and easiness to use;

glutaraldehyde, periodic acid,

N-succinimidyl-2-maleimidoacetic acid,

N-succinidyl-4-maleimidobutyric acid,

N-succinidyl-6-maleimidohexanoic acid,

N-succinidyl-4-maleimide methylcyclohexane-1-carboxylic acid,

N-sulfosuccinidyl-4-maleimide methylcyclohexane-1-carboxylic acid,

H-succinidyl-4-maleimidomethylbenzoic acid,

N-succinidyl-3-maleimidobenzoic acid,

N-succinidyl-4-maleimidophenyl-4-butyric acid,

N-sulfosuccinidyl-4-maleimidophenyl-4-butyric acid,

N,N'-oxydimethylene-dimaleimide,

N,N'-o-phenylene-dimaleimide,

N, N'-m-phenylene-dimaleimide,

N,N'-p-phenylene-dimaleimide,

N,N'-hexametylene-dimaleimide,

N-succinidyl maleimide carboxylic acid,

N-succinidyl-S-acetylmercaptoacetic acid,

N-succinidyl-3-(2-pyridyldithio)propionate,

S-acetylmercaptosuccinic anhydride, methyl-3-(4'-dithiopyridyl)propionimidate, methyl-4-mercaptobutylimidate, methyl-3-marcaptopropionimidate, iminothiolene, o-carboxymethyl-hydroxylamine, azodiphenylbylmaleimide, bis(sulfosuccinimidyl) suberate, 4,4'-diisothiocyano-2,2'-stilbenedisulfonic acid, 4,4'-difluoro-3,3'-dinitrodiphenyl sulfone, 1,5-difluoro-2,4-dinitrobenzene, p-phenylenediisothiocyanate, dimethyladipimidate, dimethylpimelimidate, dimethylsuberimidate, p-azidophenacylbromide, p-azidophenylglyoxal, N-hydroxysuccinimidyl-4-azidobenzoate, 4-fluoro-3-nitrophenylazide, methyl-4-azidobenzoimidate, N-5-azido-2-nitrobenzoiloxysuccinimide, N-succimidyl-6-(4'-azido-2'-nitrophenylamino)hexanoate, 1,4-benzoquinone, N-succinimidyl-3-(2'-pyridyldithio)propionate N-(4-maleimidobutyryloxy)sulfosuccinimide, sodium salt, N-(6-maleimidocaproyloxy)sulfosuccinimide, sodium salt, N-(8-maleimidocaproyloxy)sulfosuccinimide, sodium salt, N-(11-maleimidocaproundecanoyloxy) sulfosuccinimide, sodium salt, N-[2-(1-piperazinyl)ethyl]maleimide, dihydrochloride, bisdiazobenzidine, hexamethylenediisocyanate, toluenediisocyanate, hexamethylene diisothiocyanate, N,N'-ethylene bismaleinimide, N,N'-polymethyleneisoiodoacetamide, 2,4-dinitrobenzensulfonate, sodium salt, carbodiimide derivatives whose condensed agent is expressed by RN=C=NR (or R') or diazo compounds, N-hydroxysuccinimide, tri-n-butylamine, butylchloroformate, isobutyl isocyanide.

By employing a plasma-polymerized membrane, the present invention enables the provision of highly uniform biosensors. As a result, the biosensor can be supplied as a small chip. For example, there is a known technique in which microgrooves are made on a silicon board with plasma etching, and metal electrode patterns are formed inside the microgrooves that also serve as flowcells for micro-volume liquid specimens (Analytical Chemistry 65, 2731–2735, 1993# Analytical Chemistry 69, 253–258, 1998). The present invention may be applied to such microchips to construct biosensor tips. For example, the above-mentioned microgrooves with metal electrode patterns are covered with a plasma-polymerized membrane and a catalytic substance is immobilized on the membrane. By introducing a micro-volume liquid specimen into the grooves using a similar technique used for known microchips, analysis is performed by the action of the catalytic substance. Since the present invention employs a plasma-polymerized membrane, a uniform plasma-polymerized membrane can be made without altering minute structures of the microchip.

The biosensor of the present invention can also be applied to indwelling sensors. For example, an indwelling sensor for real-time monitoring of blood glucose level and automatic supply of insulin according to the measurement is publicly known (Blomedica, Hokuryukan, Vol. 5 No. 5, 458–466, 1990). Use of the biosensor of the present invention in such sensors improves safety, because the biosensor does not use mediators that might show toxicity, and the possibility of the elution of the catalytic substance immobilized on the sensor is low. The present invention also has an advantage in that it is capable of applying a uniform coating with plasma-polymerized membrane even to a needle-shaped structure.

(Description of signs) 1: Board, 2; Plasma-polymerized membrane, 3: Platinum electrode patterns, 4: Plasma-polymerized membrane, 5: Enzyme

BEST MODE FOR CARRYING OUT THE INVENTION

Following describes the present invention in detail based on Examples.

EXAMPLE 1

Figure 1:
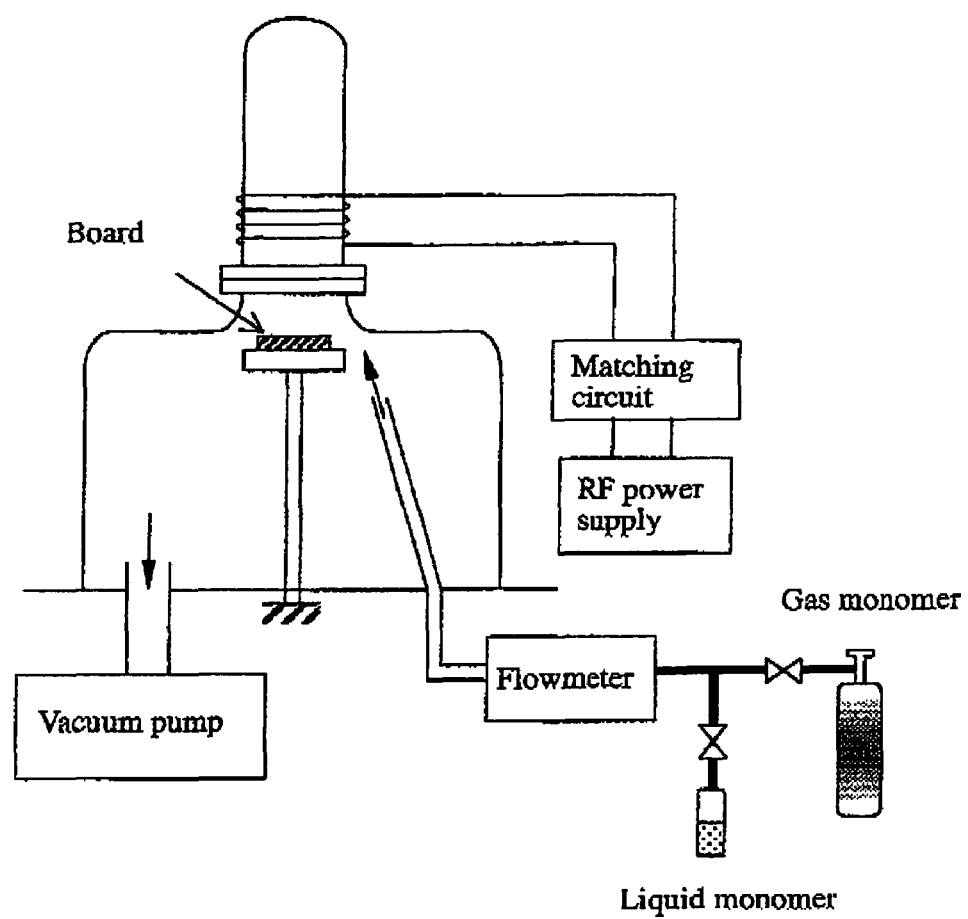
FIG. 1 shows a typical plasma-polymerized membrane system.
Figure 2:
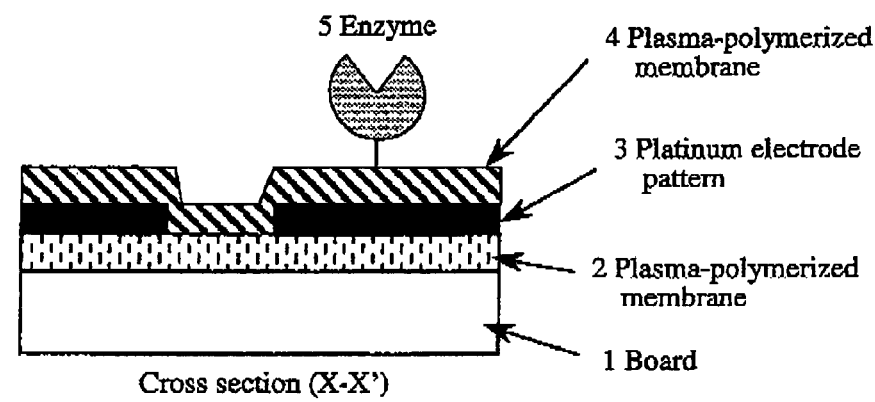
FIG. 2 shows a cross-section and exploded top views of the biosensor of the present invention.
Figure 2:
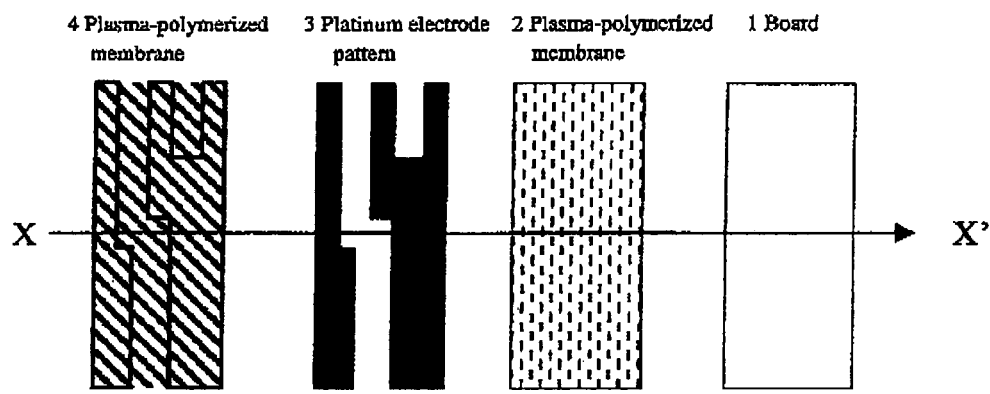

This is an example of a biosensor of the present invention, a glucose sensor using GOD. Structure of the glucose sensor of the present invention is shown in FIG. 2. The manufacturing process was as follows: A glass board was washed and an approximately 100 nm-thick plasma-polymerized membrane (1) was formed on the board using hexamethyldisiloxane. Conditions for plasma polymerization were as follows:

Flow rate: 15 cm$^3$/min,

Discharge power: 40 W,

Pressure: 4.6 Pa,

Discharge time: 1 min.

Then, an approximately 100 thick platinum electrode pattern (2) was formed with the spatter method using a mask. The mask was removed and then an approximately 50 nm-thick acetonitrile plasma-polymerized membrane was formed. Conditions for this plasma polymerization were as follows:

Flow rate: 15 cm$^3$/min,

Discharge power: 80 W,

Pressure: 2 Pa,

Discharge time: 1 min.

Amino groups are present at a high density on the surface of this membrane. Using these amino groups, the enzyme was immobilized with glutaraldehyde, a crosslinking agent. After dropping 1% glutaraldehyde solution on the surface, the membrane was left to stand for approximately 20 minutes. After washing with distilled water, 10 mg/mL glucose oxidase solution (pH 7, 50 mM, phosphate buffer) was dropped onto the membrane. In addition, 0.1% glutaraldehyde solution was dropped. After approximately 20 minutes, the sensor was washed thoroughly with distilled water. The principle of detection of this biosensor is as follows: First, glucose-specific oxidation reaction by glucose oxidase (the first reaction) starts. Then, $H_2O_2$ generated by the first reaction passes through the plasma-polymerized membrane and is electrochemically detected on the platinum electrode (the second reaction). First reaction: Glucose+Oxygen->Gluconolactone+$H_2O_2$ Second reaction: $H_2O_2$->$2H^+$+Oxygen+$2e^-$ Here only $H_2O_2$, whose size is small, passes through the plasma-polymerized membrane while other contaminants contained in blood do not. Therefore, the glucose concentration is effectively detected as changes in current without being effected by such substances as ascorbic acid and uric acid that are known as interfering components when using known biosensors. Also, as described later, $H_2O_2$ has a larger diffusion coefficient against the inside of plasma-polymerized membrane of acetonitrile than in the solution bulk state, causing a faster electrode reaction. This result indicates that the biosensor of the present invention reacts to glucose without being saturated even at higher concentration ranges.

The whole manufacturing process of such a biosensor can be done using dry processes, except for the final step of immobilizing enzymes. In some cases, processes from metal electrode pattern formation to plasma-polymerized membrane formation can be completed in the same chamber. Such a manufacturing process improves reproducibility of the sensor characteristics enabling reduction of costs and high-quality mass production.

Ultra-minification is also easy with this biosensor. In addition, minification is expected to relatively increase the efficiency of the electrochemical detection. This is because, in general, objects in spectroscopic detection decrease in proportion to the third power of size, whereas objects in electrochemical detection decrease in proportion to the second power of the size. Further, the detection method of the present invention uses electrochemical detection; this makes the system smaller and as a result, suppresses consumption of reagents and specimens. Indwelling sensors can also be realized with this invention since the biosensor of this invention does not use toxic substances such as mediators.

Figure 3:
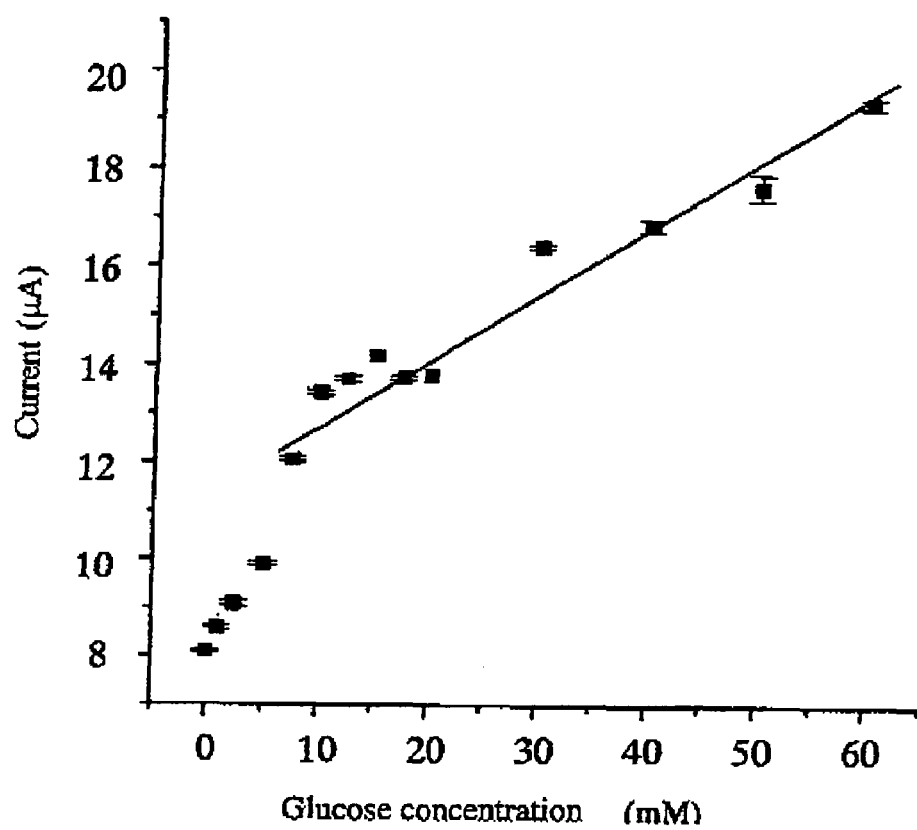
FIG. 3 shows the calibration curve with the biosensor of the present invention. The vertical axis indicates change in current ($\mu$A) and the horizontal axis glucose concentration (mM).

Glucose concentrations were actually measured using the glucose sensor obtained with this embodiment. The above-mentioned biosensor was contacted to glucose solutions of different concentrations (0–60 mM). With cyclic voltametry, measurement was performed using silver/silver chloride in the range of 0–1 V at the sweep rate of 50 mV/sec. The oxidation current was set at 500 mV. The results are shown in FIG. 3, which indicates oxidation currents and glucose concentrations. The currents appear to have preferable linearity in the range of 5–60 mV. This exceeds by far the linearity (5.6–33.6 mM) obtained with the glucose sensors described in JP-A Hei 1-253648, JP-B Hei 5-24453, JP-A Hei 6-213858, JP-A Hei 1-156658, JP-B Hei 6-58338 and JP-A Sho 63-139243. The detection limit is 0.04 mM (S/N ratio 3), higher than that of conventional sensors. In glucose sensors without a plasma-polymerized membrane, the sensor's current response values appear to be low because of a lower amount of immobilized enzymes (immobilized with gamma-amino-trimethoxysilane). This result appears to indicate that preferable linearity is obtained even in higher glucose concentration ranges because the enzymes are immobilized in high density on the approximately 100 nm-thick plasma-polymerized membrane over the thin platinum membrane, making the distance between enzyme reaction sites and the electrode extremely close.

Figure 4:
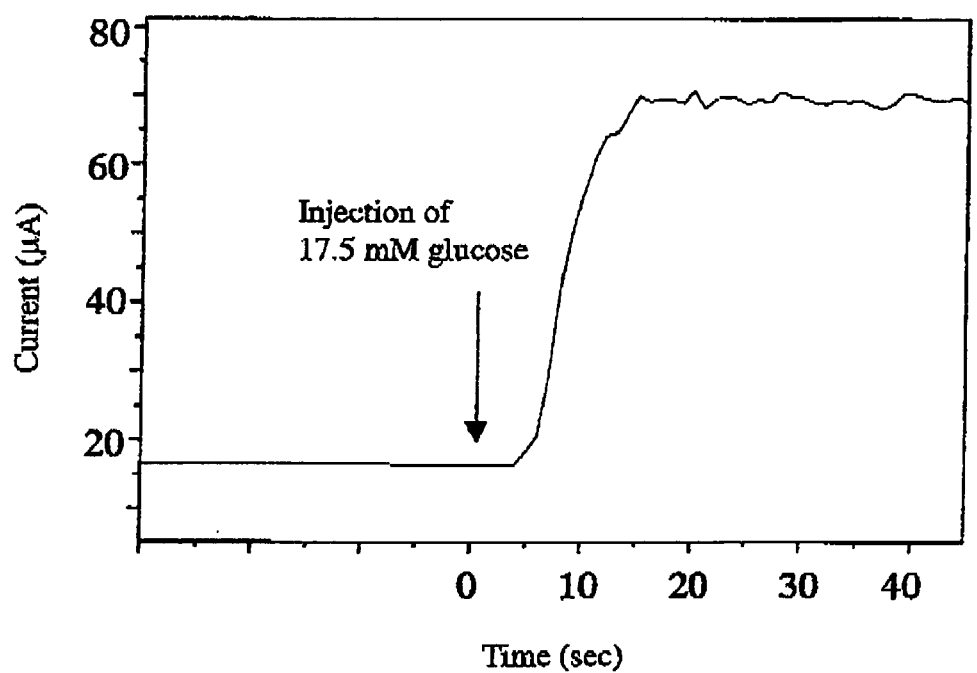
FIG. 4 shows the time response curve of the biosensor of the present invention to glucose. The vertical axis indicates change in current ($\mu$A) and the horizontal axis time (sec.).

Next, response characteristics of the biosensor of the present invention to a glucose solution were compared to those of a biosensor with a publicly known structure. Result is shown in FIG. 4, which shows change in current with time by enzyme reactions at a constant voltage of 500 mV. The glucose concentration was 17.5 mM. It required approximately 15 seconds before reaching a steady state. Compared to the glucose sensor described in JP-B Hei 5-24453, which requires more than 30 seconds to respond, the biosensor of the present invention has an extremely higher response speed. This may be attributed to the very short distance between the enzyme reaction and the electrode reaction sites.

Further, with a biosensor prepared in the present invention, effects of various contaminants on the sensor's normal response to 1 mM glucose were investigated. Contaminants shown in Table 1 were added to 1 mM glucose solution and their effects on response of the biosensor of the present invention were observed. Results are shown in Table 1, which indicates that effects of contaminants were suppressed by the plasma-polymerized membrane.

TABLE 1

| Contaminant Concentration (mM) | Ascorbic acid | | Uric acid | | Acetaminophen | |
| --- | --- | --- | --- | --- | --- | --- |
| | Without membrane | With membrane | Without membrane | With membrane | Without membrane | With membrane |
| 0.1 | 12.6 | −14.1 | −1.97 | −4.68 | 27.0 | 1.70 |
| 0.2 | 22.9 | −10.6 | −7.38 | −5.23 | 51.0 | 20.4 |
| 0.3 | 33.0 | −1.35 | −14.1 | −5.77 | 77.2 | 38.9 |
| 0.6 | 48.2 | 23.5 | −3.94 | −5.95 | 141 | 84.5 |
| 0.9 | 92.1 | 46.2 | −7.29 | −6.49 | 238 | 150 |
| 1.2 | 106.8 | 68.2 | 9.31 | −9.01 | 321 | 199 |

Currents were calculated by (I2-I1)/I1×100; I1 is current for glucose 1 mM only, I2 is current for glucose 1 mM+other contaminants. Without membrane: where enzyme was immobilized in the absence of plasma-polymerized membrane.

With membrane: where enzyme was immobilized in the presence of plasma-polymerized membrane.

EXAMPLE 2

Figure 5:
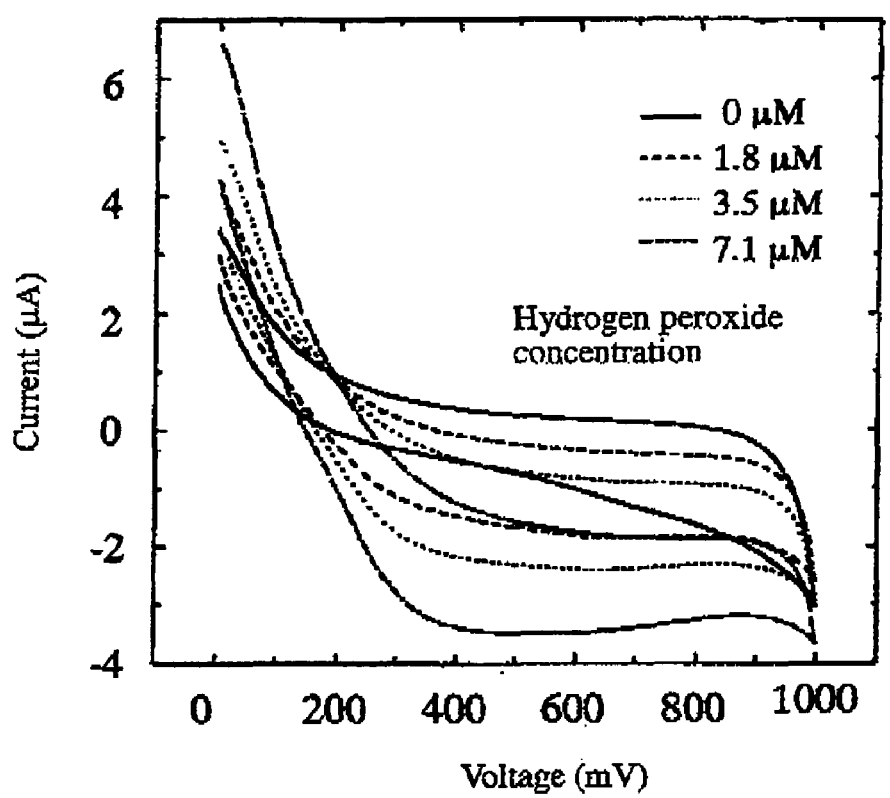
FIG. 5 is a cyclic voltamogram of a platinum electrode pattern formed on a plasma-polymerized membrane showing the electrode response to $H_2O_2$. The vertical axis indicates current ($\mu$A) and the horizontal axis voltage (mV).

Electrode response characteristics of the platinum electrode pattern on the plasma-polymerized membrane were examined. With the glucose sensor shown in FIG. 2, with the board (1), plasma-polymerized membrane (2) and thin platinum membrane (3) and without immobilizing enzyme, responses to $H_2O_2$ of different concentrations were measured. Results are shown in FIG. 5. Silver/silver chloride was used for the reference electrode. Sweep rate was 50 mV/s. The result indicates that the platinum electrode of the present invention shows a favorable electrode response to $H_2O_2$. Also, it does not detach even after being immersed in the solution for a long period of time. Thus, the platinum electrode formed on the surface of the plasma-polymerized membrane has sufficient characteristics as an electrode for a biosensor. In contrast, platinum electrodes formed on glass or plastic boards detach easily when immersed in water.

EXAMPLE 3

Presence of amino groups on the acetonitrile plasma-polymerized membrane (4) was confirmed. To confirm presence of amino groups on the surface of the membrane, the following experiment was conducted: the membrane surface was exposed to vapor of pentafluorobenzaldehyde, an agent that specifically reacts with amino groups, for 8 hours and then x-ray photoelectron spectroscopy was performed. As a result, approximately 7% or more fluorine atoms were detected on the surface. The presence of fluorine atoms of the modulating agent indicates that pentafluorobenzaldehyde has specifically reacted with amino groups on the membrane surface. It means that amino groups are present at a high density on the surface of the acetonitrile plasma-polymerized membrane. These amino groups can be used to immobilize enzymes covalently.

EXAMPLE 4

Figure 6:
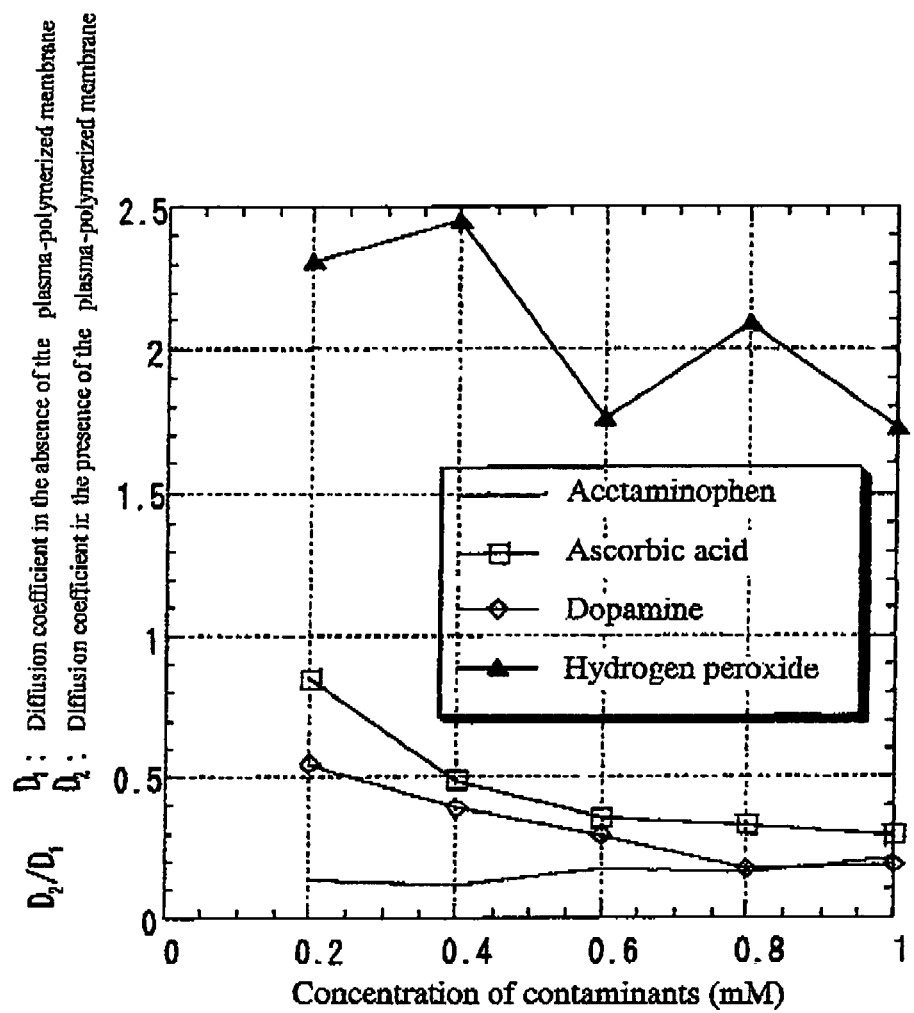
FIG. 6 shows diffusion coefficients of various contaminants contained in a plasma-polymerized membrane formed using acetonitrile as the monomer gas. The vertical axis indicates diffusion coefficients: D2 for when plasma polymerization is present, D1 for when plasma polymerization is absent. The horizontal axis indicates concentration of the substances (mM).

The following experiment was conducted to examine the size effect of the plasma-polymerized membrane. Like Example 2, a device without enzyme immobilization was used and diffusion coefficients of different contaminants in the membrane were determined with chronocoulometry. As contaminants, $H_2O_2$, vitamin C, dopamine and acetaminophen were used. Results are shown in FIG. 6. Ratios of diffusion coefficients in the device with a plasma-polymerized membrane formed on the platinum electrode pattern to those in th device without a plasma-polymerized membrane exposed to the platinum electrode pattern were 1.8–2.4 with $H_2O_2$ while approximately 0.1–0.5 with other substances. Considering the molecular sizes, this result supports the fact that the plasma-polymerized membrane functions as a selective membrane for $H_2O_2$ due to the size effect. Further, the fact that the diffusive coefficient of $H_2O_2$ has become two folds or more than when the platinum electrode is exposed, means that the acetonitrile plasma-polymerized the membrane has a tendency to selectively pass $H_2O_2$.

INDUSTRIAL APPLICABILITY

The glucose sensor using the plasma-polymerized membrane of the present invention has the following advantages: its performance is equal or superior to that of currently available glucose sensors, and the manufacturing process is easier.

To extend the application of such quick and simple biosensors, a biosensor system has to be established with technologies that enable miniaturization, integration and mass production. Micro-machining is an example of such technologies. The present invention employs dry processes and thus can be easily combined with micro-machining technologies.

A miniaturized sensor can be placed within the body to perform continuous measurement. The biosensor of the present invention is suitable for this purpose because it can not only be downsized, but it is also safer because the enzyme need not be mediator modified. The plasma-polymerized membrane, unlike other organic membranes, is an ultra-thin membrane that has a high denseness with a high crosslinking rate. By utilizing this plasma-polymerized membrane, the biosensor of the present invention has the following advantages: First, it eliminates effects of other contaminants by selectively passing $H_2O_2$ by its size effect and ion functional effect. Second, the plasma-polymerized membrane is an ultra-thin membrane with an approximately 100 nm thickness and thus enables the immobilization of enzymes close to the electrode. This enables an efficient reaction between the reaction products and the electrode, a faster reaction, and the ability to measure a high-density substrate (glucose). Lastly enzymes can be immobilized at a high density because the plasma-polymerized membrane allows introduction of such functional groups such as amino and thiol groups at a high density for enzyme immobilization.

The plasma-polymerized membrane is highly adhesive to the metal electrode pattern and can be made thinly and uniformly with a high reproducibility. Also, the easy manufacturing process and easy combination with the semiconductor processing technologies enables ultra-miniaturization.

What is claimed is:

1. A biosensor comprising the following elements:
   (a) first and second plasma-polymerized membranes, wherein said first plasma-polymerized membrane is an acetonitrile plasma polymerized membrane,
   (b) a catalytic substance immobilized on the first plasma-polymerized membrane, and
   (c) a metal electrode pattern in contact with a test sample only via the first plasma-polymerized membrane, wherein said metal electrode pattern is in direct contact with the first and second plasma-polymerized membranes, such that the first plasma-polymerized membrane is above and the second plasma-polymerized membrane is below the metal electrode pattern, said second plasma-polymerized membrane being formed from an organic silicon compound.

2. The biosensor according to claim 1, wherein the catalytic substance is covalently bound to the first plasma-polymerized membrane with a crosslinking agent.

3. The biosensor according to claim 1, wherein the catalytic substance is an enzyme.

4. The biosensor according to claim 3, wherein the enzyme is either an oxidase or a dehydrogenase.

5. The biosensor according to claim 4, wherein the enzyme is an oxidase which is selected from the group consisting of glucose oxidase, galactose oxidase, pyruvate oxidase, D- or L-amino acid oxidase, amine oxidase, cholesterol oxidase, and choline oxidase.

6. The biosensor according to claim 4, wherein the enzyme is a dehydrogenase which is selected from the group consisting of alcohol dehydrogenase, glutamic acid dehydrogenase, cholesterol dehydrogenase, aldehyde dehydrogenase, glucose dehydrogenase, fructose dehydrogenase, sorbitol dehydrogenase, and glycerol dehydrogenase.

7. The biosensor according to claim 1, comprising a multi-layer structure in which one or more layers of plasma-polymerized membranes are overlaid on the first plasma-polymerized membrane.

8. The biosensor according to claim 7, wherein the overlaid one or more layers of plasma-polymerized membranes comprises a functional group, said functional group formed by a polymerizing reaction of a monomer gas dispersed in plasma.

9. The biosensor according to claim 8, wherein the monomer gas is selected from the group consisting of nitrogen, ammonia, hydrazine, hydrogen sulfide, hydrogen disulfide, oxygen, hydrogen, water, and halogen gas.

10. A method for measuring a substrate in a test sample using a biosensor, wherein the biosensor comprises (i) a metal electrode pattern that contacts a test sample only via a plasma-polymerized membrane, wherein the metal electrode pattern is in direct contact with first and second plasma-polymerized membranes, wherein said first plasma polymerized membrane is an acetonitrile plasma polymerized membrane and said second plasma-polymerized membrane is formed from an organic silicon compound, and (ii) a catalytic substance immobilized on the first plasma-polymerized membrane, and wherein said method comprises the following steps of:
   (a) contacting the test sample with the biosensor, and,
   (b) detecting electrical changes that occur as a result of the reaction between the catalytic substance and substrate using the metal electrode patterns;
   (c) measuring the substrate based on the electrical charges.

11. A biosensor comprising:
   a. first and second plasma-polymerized membranes, wherein said first plasma-polymerized membrane is an acetonitrile plasma polymerized membrane;
   b. a catalytic substance immobilized on the first plasma-polymerized membrane; and,
   c. a metal electrode pattern in direct contact with the first and second plasma-polymerized membranes, such that the first plasma-polymerized membrane is above and the second plasma-polymerized membrane is below the metal electrode pattern; wherein the first plasma-polymerized membrane covers the metal electrode pattern, preventing a specimen from directly contacting the metal electrode pattern and said second plasma-polymerized membrane is formed from an organic silicon compound.

12. A biosensor comprising:
   a. first and second plasma-polymerized membrane, wherein said first plasma-polymerized membrane is an acetonitrile plasma polymerized membrane;
   b. a catalytic substance immobilized on the first plasma-polymerized membrane; and,
   c. a metal electrode pattern in direct contact the first and second plasma-polymerized membranes, such that the first plasma-polymerized membrane is above and the second plasma-polymerized membrane is below the metal electrode pattern, said second plasma-polymerized membrane being formed from an organic silicon compound;

wherein the first plasma-polymerized membrane covers a surface of a board containing the metal electrode pattern, preventing a specimen from directly contacting the metal electrode pattern.

13. A biosensor comprising:
a. first and second plasma-polymerized membrane, wherein said first plasma-polymerized membrane is an acetonitrile plasma polymerized membrane;
b. a catalytic substance immobilized on the first plasma-polymerized membrane;
c. a metal electrode pattern in direct contact with the first and second plasma-polymerized membranes, such that the first plasma-polymerized membrane is above and the second plasma-polymerized membrane is below the metal electrode pattern, said second plasma-polymerized membrane being formed from an organic silicon compound; and
d. a structure for containing a specimen;

wherein the first plasma-polymerized membrane is interposed between the structure and the metal electrode pattern and prevents a specimen from directly contacting the metal electrode pattern.

14. The biosensor of claim 13, wherein the structure is a groove.

15. A method of manufacturing a biosensor, the method comprising:

forming a metal electrode pattern layer;

depositing a first plasma-polymerized membrane layer over said metal electrode pattern layer so as to cover all exposed portions of said metal electrode pattern layer, wherein said first plasma-polymerized membrane is an acetonitrile plasma polymerized membrane;

depositing a second plasma-polymerized membrane layer over said metal electrode pattern layer such that the first plasma-polymerized membrane is above and the second plasma-polymerized membrane is below the metal electrode pattern said second plasma-polymerized membrane being formed from an organic silicon compound;

immobilizing a catalytic substance on the first plasma-polymerized membrane layer.

16. The method of claim 15, wherein said step of forming a metal electrode pattern layer comprises forming the metal electrode pattern layer on a board, wherein the second plasma-polymerized membrane is disposed between the metal electrode pattern layer and the board.

17. The method of claim 15, wherein the second plasma-polymerized membrane is formed on a board.

* * * * *